United States Patent
Shatkina et al.

(10) Patent No.: US 8,142,823 B2
(45) Date of Patent: Mar. 27, 2012

(54) NUTRACEUTICAL COMPOSITION

(76) Inventors: Rufina Shatkina, Orem, UT (US); Sam D Gurevich, Orem, UT (US)

( * ) Notice: Subject to any disclaimer, the term of this patent is extended or adjusted under 35 U.S.C. 154(b) by 213 days.

(21) Appl. No.: 12/626,893

(22) Filed: Nov. 28, 2009

(65) Prior Publication Data

US 2010/0136064 A1    Jun. 3, 2010

Related U.S. Application Data

(60) Provisional application No. 61/119,501, filed on Dec. 3, 2008.

(51) Int. Cl.
*A01N 65/00* (2009.01)
(52) U.S. Cl. .................................................... 424/725
(58) Field of Classification Search ........................ None
See application file for complete search history.

(56) References Cited

U.S. PATENT DOCUMENTS

2009/0246231 A1* 10/2009 Valencia et al. .............. 424/400

* cited by examiner

*Primary Examiner* — Michael Meller

(57) ABSTRACT

A nutraceutical substance comprising *Adansonia digitata* (Baobab), *Borojoa patinoi* (Borojo), *Cyclanthera Pedata* (Caigua) and *Aframomum melegueta* (Grains of Paradise). In some embodiments, the whole fruit of these plants may be used. In other embodiments, roots bark, saps, roots or seeds from these plants may be used. The substance may be dried, powderized, and packaged for use directly, or processed into a pill or digestible capsule form. In other embodiments, the substance may be used as brew, water extract, alcohol extract, or pulp mixture. The substance is intended for ingestion by a human user, and may be useful to promote well-being, provide nutritional value, and aid in preventative health management. Cosmeceutical and hair care formulations employing these ingredients are also disclosed.

1 Claim, 3 Drawing Sheets

Figure 3A-C

NUTRACEUTICAL COMPOSITION

RELATED APPLICATIONS

This application claims the priority benefit of provisional application 61/119,501, "Nutraceutical Composition," filed Dec. 3, 2008.

BACKGROUND

Nutraceutical compositions (e.g. foods or naturally occurring food supplements intended for human ingestion, and thought to have a beneficial effect on human health) are commonly used for their preventative and medicinal qualities. Various nutraceuticals are recognized as providing relief from or preventing specific diseases and ailments. Such nutraceuticals may comprise a single element, such as broccoli, which contains sulphrophane commonly believed to prevent cancer. Or, alternatively, may comprise of complex combinations of substances resulting in a nutraceutical that provides specific benefits. For obvious reasons there is a constant demand for any new composition that can provide additional health benefits over existing Nutraceuticals.

Often, a combination of several substances results in unexpected benefits due to the synergistic nature of the substances. For example, substance A may be known to provide benefit X and substance B may be known to provide benefit Y. While it might be expected that a combination of A and B will result in benefits X and Y, due to the synergistic nature of the combination, benefit Z may unexpectedly be present. When useful synergistic properties are discovered in a combination of substances, the developed nutraceuticals often offer valuable health benefits not found in other substances. Additionally, nutraceuticals derived from unknown or little-known substances may offer health benefits previously unrecognized.

SUMMARY

One object of the present system and method is to provide a nutraceutical composition comprising the novel combination of portions of *Adansonia digitata* (Baobab), *Borojoa patinoi* (Borojo), *Cyclanthera Pedata* (Caigua), and *Aframomum melegueta* (Grains of Paradise). One result of such a combination is the holistic health benefits to be obtained from such a combination. Furthermore, the synergistic combination of the Baobab, Borojo, Caigua, and Grains of Paradise offers many nutraceutical benefits not present by an individual fruit or currently available nutraceutical.

According to one exemplary embodiment, the fruit of each of these trees is used in its entirety, Additionally, according to another exemplary embodiment, the leaves and fiber of the Baobab are also included in the nutraceutical. The Nutraceutical, according to anyone of the various embodiments described in detail below, serves to promote well-being, provide nutritional value, and aid in preventative health management According to one exemplary embodiment of the present system and method, the combination of Baobab, Borojo, Caigua, and Grains of Paradise is formed into a powder. The powder can then be used in a variety of manners including, being reconstituted with a beverage, sprinkled on foods, such as cereals, soups, yogurts, etc" taken in pill form or concentrate, and/or combined with a variety of foods and other substances, According to various embodiments, Baobab, Borojo, Caigua, and Grains of Paradise are each individually powdered and the various powders are then combined, Alternatively, a combination of Baobab, Borojo, Caigua, and Grains of Paradise is formed and the combination is then powdered, According to one exemplary embodiment, the inherent excipient properties of Baobab are utilized to form a combination that requires no additional excipients, This would be especially beneficial if an attempt to exclude any substance besides Baobab, Borojo, Caigua, and Grains of Paradise from the combination is desired, Alternatively, the combination may include many substances (beneficial or excipient in nature) in addition to Baobab, Borojo, Caigua, and Grains of Paradise, While according to several embodiments the whole fruit of each of Baobab, Borojo, Caigua, and Grains of Paradise is used, it is also conceivable to exclude any portion or portions of one or more of the substances, It is also conceivable to include additional portions of each of the plants beyond the fruit, such as the bark, leaves, roots, saps, and other portions of the plants,

DETAILED DESCRIPTION

Figure 1:
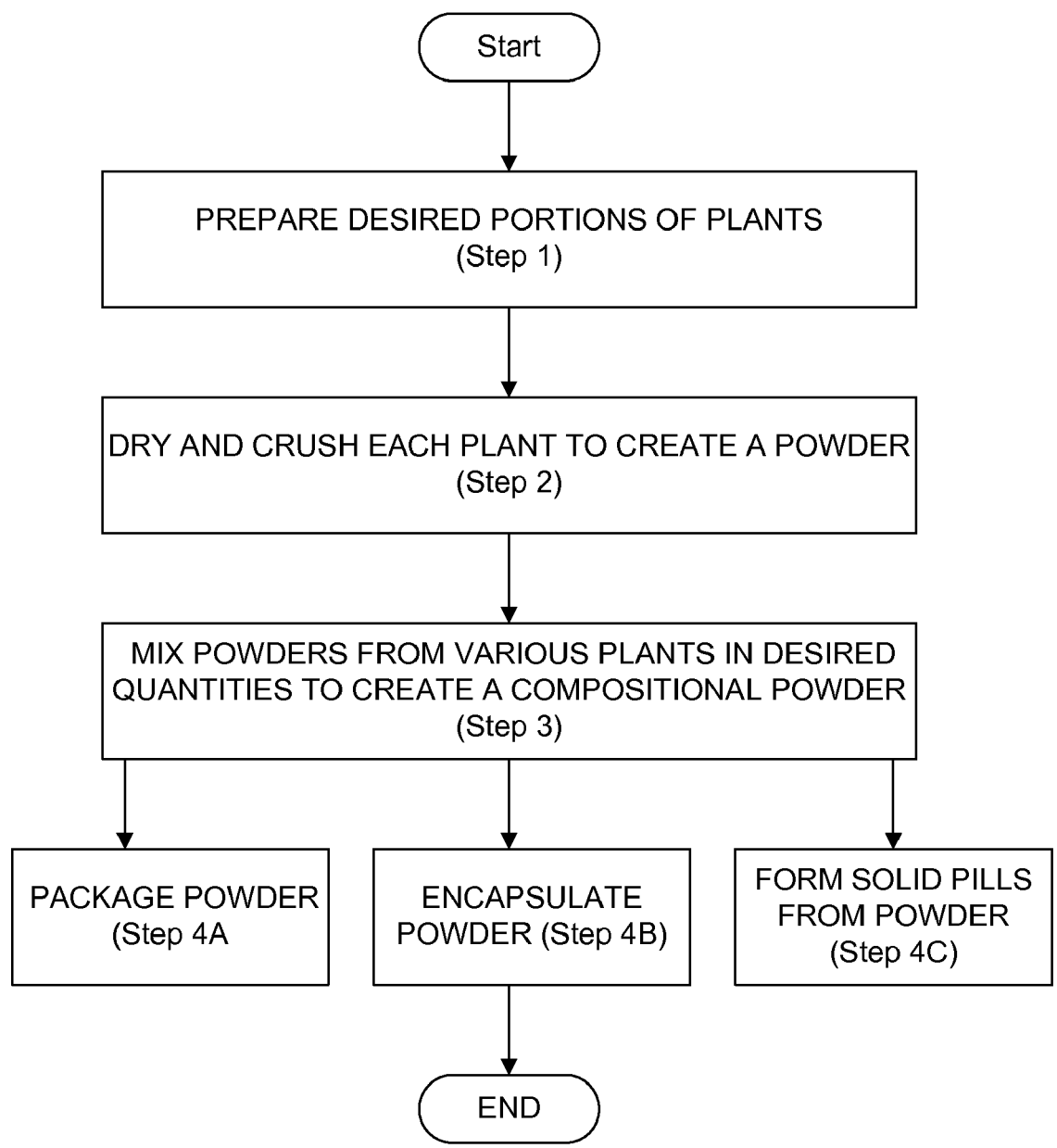
FIG. 1 illustrates a flow chart of the formation of a nutraceutical, according to one exemplary embodiment of the present system and method.

As has been presented, a primary object of the present system and method is to form a nutraceutical comprising of portions of *Adansonia digitata* (Baobab), *Borojoa patinoi* (Borojo), *Cyclanthera Pedata* (Caigua), and *Aframomum melegueta* (Grains of Paradise). Each of these plants is known to have nutritional and medicinal value. However, the present system and method provides a novel manner of combining portions of the plants resulting in synergistic health benefits otherwise unavailable. Furthermore, the present system and method provides a nutraceutical in a powder form, which allows a user to easily obtain the benefits thereof.

Without wishing to be bound by a particular theory, applicants believe that the formulation described herein may potentially be useful as a dietary supplement for individuals suffering from diabetes, and other related medical problems, such as high cholesterol and high blood pressure, cardiovascular disease, inflammatory diseases, obesity, stress related disorders, low energy, loss of libido, and impotence.

Baobab (*Adansonia digitata*) is an African plant. Its fruit has a high concentration of Vitamin C (300 mg/100 g). It is also a good source of soluble fibers with prebiotic-like activity in vitro. Due to its prebiotic and probiotic activity, it is used as an intestinal regulator in cases of gastric disorders (for both constipation and dysentery). It is also a good source of micronutrients such as bio-flavonoids, and alpha-linolenic acid (an omega 3 fatty acid, which generally promotes cardiovascular health), as well as carbohydrates such as glucose, fructose, saccarose, maltose, soluble polysaccharides, and starch. Baobab fruit is used in Africa for its anti-inflammatory, analgesic, and antipyretic activity.

By contrast, Borojo (*Boroja patinoi*) is a South American plant. It contains a high percentage of fructose and glucose, as well as high levels of both water-soluble B vitamins, amino acids, and protein. Is often used by the natives as their main source of energy on long journeys through the jungle. It also has a native reputation for possessing some medicinal properties, and is locally used as an aphrodisiac by both men and women.

Caigua (*Cyclanthera pedata*) is another plant native to South America. The cucumber-like fruits of this plant are used in South America for their anti-inflammatory, hypoglycemic and hypocholesterolemic properties. The plant contains vegetal sterols (for example phytosterol) that positively influences absorption of cholesterol, and has been shown to lower harmful LDL cholesterol levels in humans, while raising the level of HDL cholesterol.

Grains of Paradise (also called *Aframomum meleguetta* pepper, or *Aframomum*) is a spice native to tropical West Africa. In Ghana, the seeds are widely used in spicing meat, sauces and soups and mixed with other herbs for the treatment of body pains and rheumatism.

*Aframomum* has been used in various herbal medicinal formulas. The seed is ground into a soft paste and this paste has been observed to have antibiotic properties. In particular, the essential oil of *Aframomum* has exhibited activity against gram positive and gram-negative bacteria, as well as the pathogenic yeast Candida albicans.

Formulation Discussion:

The formulation, composition, or substance of this invention may be prepared in a number of ways, including as a dry powder, as a capsule, as a ready to drink juice or as a food additive. Alternatively, the formulation may also be brewed, fermented, boiled to create a compote, prepared as an alcohol or water extract. In general, any formulation using any combination of Baobab, Borojoa, Caigua and Grains of Paradise prepared in any manner will be within the spirit of the invention.

Here various dry formulation compositions will be described first.

Referring first to FIG. 1, an initial step to creating a nutraceutical is the preparation of the desired portions of the plants (Step 1). According to various embodiments, this includes harvesting, shipping, removing undesired portions, washing, opening, separating, and any additional steps that must be taken prior to drying. Each plant, Baobab, Borojo, Caigua, and Grains of Paradise can then be dried and powdered. The drying process may be preformed according to the needs of each individual plant. Conventional methods of drying may be used that involve naturally drying with sun. Alternatively they may be dried using specialized ovens. Once dry, the various plants may be crushed and powderized (Step 2).

Quantities of the various powders can then be combined resulting in a desired composition (Step 3). According to one exemplary embodiment, the powders are combined using equal amounts of powder from each plant. Alternative embodiments, utilize various quantities of each powder. According to one exemplary embodiment, the quantity of one powder may be substantially greater than the quantity of another powder. The amount of each powdered plant used to create the final composition may be tailored specifically for a particular use. For example, for a high content of a specific vitamin, more of one plant may be used than another.

Once combined, the final nutraceutical (See FIG. 3A) may be packaged and sold as a powder (Step 4A). The powder may then be reconstituted with water or blended with foods and thereby be ingested for medicinal, preventive, nutritional, or otherwise health related purposes. Alternatively the powder may be encapsulated (See FIG. 3B, Step 4B). The nutraceutical capsule may then be swallowed, or broken open to be used as the powder described above. Finally, the powder can be formed into a solid pill (FIG. 3C, Step 4C). The solid pill can be dissolved in water for intake, crushed into a powder as described above, or it can be swallowed.

Figure 2:
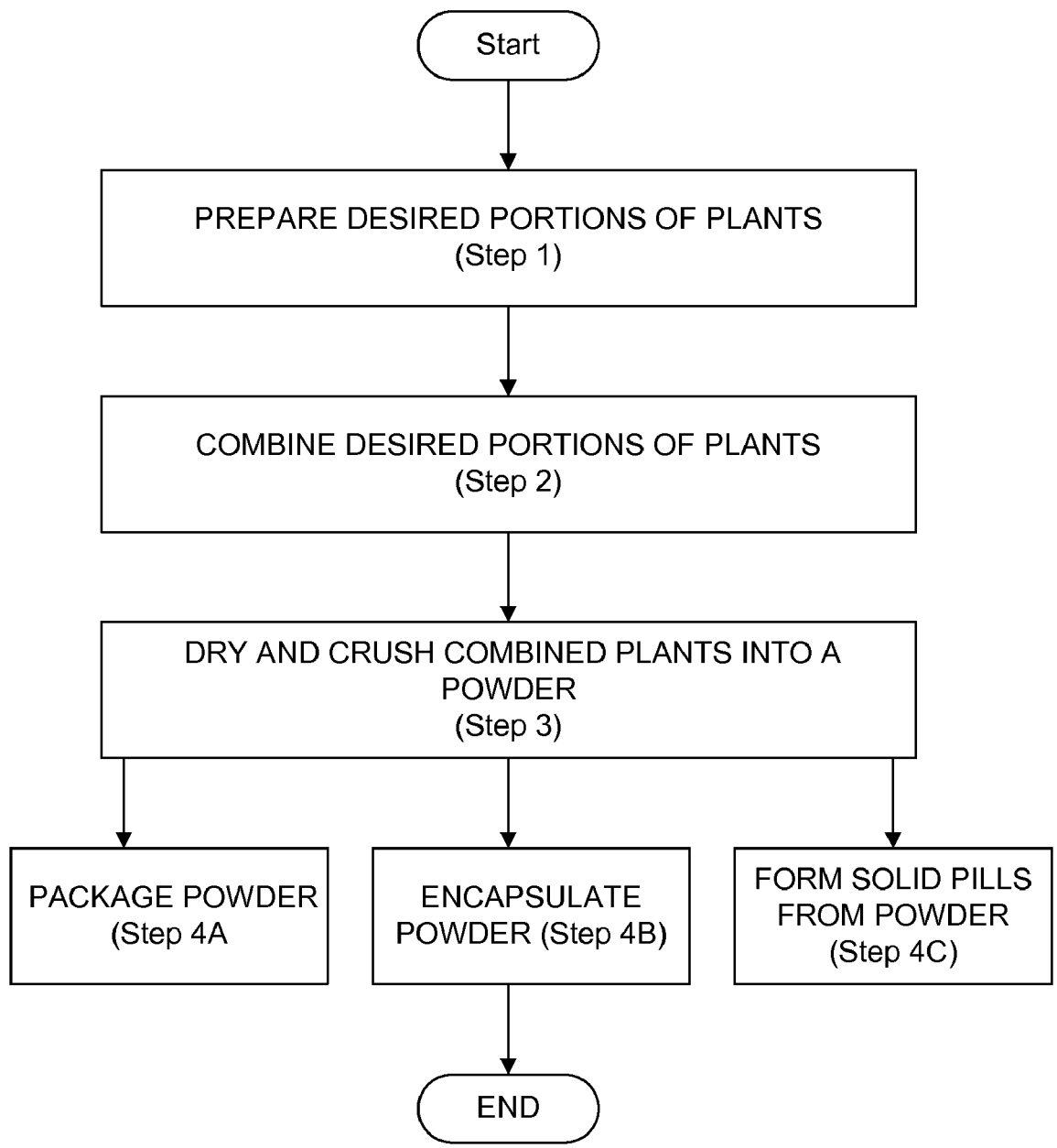
FIG. 2 illustrates an alternative method of forming a nutraceutical, according to one exemplary embodiment of the present system and method.

FIG. 2 illustrates a flow chart with a slightly different initial approach resulting in substantially the same nutraceutical. According to this method of creating the nutraceutical, the desired portions of the plant are first prepared for combining (Step 1). Subsequently the plants are mixed, resulting in a liquid or semi-liquid nutraceutical (Step 2). According to this embodiment, the nutraceutical may be sold as fresh pulp, frozen and sold, combined with water or other juices and bottled, or it may be dried and crushed into a powder (Step 3). Assuming it is dried and crushed into a powder it can then be processed and used as is described above with reference to Steps 4A-C.

Figure 3A:
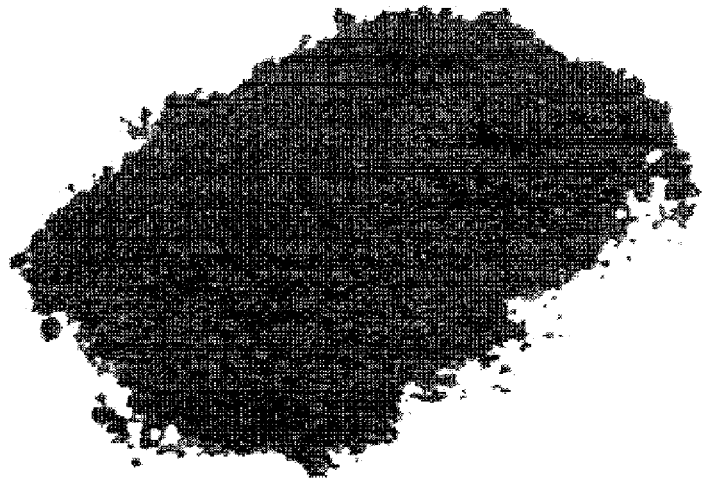
FIG. 3A-C show a nutraceutical in various forms including powder, encapsulated powder, and pill form.
Figure 3B:
Figure 3C:
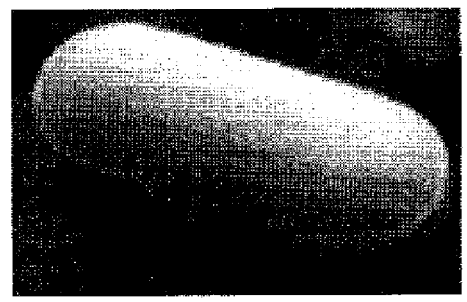

FIG. 3A illustrates a powder, according to one exemplary embodiment. While this represents the powder according to one embodiment, it is clear that the powder may range in colors, texture, and granular size. FIG. 3B illustrates an encapsulated powder, according to one exemplary embodiment. As is common with encapsulated powders, the quantity, type, and other information may be imprinted on the capsule. Finally FIG. 3C illustrates a solid pill form of the Nutraceutical, according to one exemplary embodiment.

Various embodiments may include different shapes, sizes and impressed or printed information.

Although any formula comprising a mixture of Baobab, Borojoa, Caigua, and Grains of Paradise is within the overall scope of the invention, in a preferred embodiment, the ratios of the various ingredients, by dry weight, are Baobab 40-60%, Borojoa 35-55%, Caigua 15-25% and Gains of Paradise 2-17%. One specific example of such a formula is Baobab 45%, Borojoa 35%, Caigua 15%, and Grains of Paradise 5%.

Alternatively, if the amount of Baobab present in the formulation is defined to be 1×, then the relative amounts of Borojoa, Caigua, and Grains of Paradise will preferably be in the range of Borojoa 0.58× to 1.375×, Caigua 0.25× to 0.625×, and Grains of Paradise 0.033× to 0.425×.

It should be appreciated that when the formulation is then added to water, a beverage, or other diluent, then the final percentages of the various ingredients will be diminished proportionally; however the overall ratio of the various ingredients (Baobab, Borojoa, Caigua, and Grains of Paradise) relative to each other will generally be preserved.

In addition to the dry powder and capsule formulations, and use in juice and beverage applications discussed previously, the formula may also be used in other ways.

In one alternative embodiment, the formula may be boiled to create a compote. In an alternative embodiment, the formula may be used for brewing and/or fermenting for a beer or other fermented beverage. In either of these cases, one or more types of sugar may be added to the formulation to facilitate the compote formation or the fermenting process.

In other embodiments, rather than drying down the ingredients, the fresh pulp of the ingredients may alternatively be mixed to form a juice or beverage. In this embodiment, it may be useful to store and ship the fresh pulp mixture in a frozen form, and thaw when consumption is desired. Here, in a preferred embodiment, the same general range of Baobab 40-60%, Borojoa 35-55%, Caigua 15-25% and Gains of Paradise 2-17% will be preserved, but the composition will be by liquid weight rather than by dry weight.

In still other embodiments, one or more of the Baobab, Borojoa, Caigua, and Grains of Paradise components may be added to the formula as a water or alcohol extract, brew, or fermented tincture. For example, in one alternative embodiment, the Baobab, Borojoa and Caigua components may be added to the formulation in powder form, and the Grains of Paradise component may be added to the formulation as a water or alcohol brew or extract. This mixture in turn may then be added to additional water or juices to form a beverage.

It should be appreciated that formulas in which the Baobab, Boroja, Caigua and Grains of Paradise components are used with other ingredients are also within the scope of the invention.

Other Uses

In yet another embodiment, formulations employing a mixture of Baobab, Borojoa, Caigua, and Grains of Paradise may also be used as an external skin care product, hair mask, hair treatment, or cosmeceutical intended for human use. In these alternative skin care and hair treatment formulations, the formulation may contain other ingredients as necessary to achieve the desired cream, lotion, face mask, hair mask, shampoo, or cleaner characteristics. Exemplary art for such formulations is disclosed in Draelos and Thaman, "*Cosmetic Formulation of Skin Care Products* (*Cosmetic Science and Technology Series Vol.* 30)", Informa Healthcare (2006).

What is claimed is:

1. A beverage consisting essentially of:
a mixture of Baobab, Borojo, Caigua, and Grains of Paradise;
wherein: the Borojoa to Baobab is in a ratio between 0.58 and 1.375, respectively;
the Caigua to Baobab is in a ratio between 0.25 and 0.625, respectively; and
the Grains of Paradise to Baobab is in a ratio between 0.033 and 0.425, respectively.

* * * * *